US010299863B2

(12) United States Patent
Grbic et al.

(10) Patent No.: US 10,299,863 B2
(45) Date of Patent: May 28, 2019

(54) METHOD AND COMPUTING UNIT FOR GENERATING A MANUFACTURING MODEL

(71) Applicant: Siemens Healthcare GmbH, Erlangen (DE)

(72) Inventors: Sasa Grbic, Princeton, NJ (US); Philipp Hoelzer, Bubenreuth (DE); Razvan Ionasec, Nuremberg (DE); Michael Suehling, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 156 days.

(21) Appl. No.: 15/179,240

(22) Filed: Jun. 10, 2016

(65) Prior Publication Data

US 2016/0371835 A1 Dec. 22, 2016

(30) Foreign Application Priority Data

Jun. 16, 2015 (DE) .................. 10 2015 210 984

(51) Int. Cl.
*G06K 9/00* (2006.01)
*A61B 34/10* (2016.01)
*A61F 2/30* (2006.01)

(52) U.S. Cl.
CPC .......... *A61B 34/10* (2016.02); *A61F 2/30942* (2013.01); *A61B 2034/102* (2016.02);
(Continued)

(58) Field of Classification Search
None
See application file for complete search history.

(56) References Cited

U.S. PATENT DOCUMENTS

2005/0131662 A1* 6/2005 Ascenzi ................ G09B 23/30
703/11
2010/0256504 A1* 10/2010 Moreau-Gaudry .........
A61B 5/0066
600/476
(Continued)

FOREIGN PATENT DOCUMENTS

WO WO 2004110309 A2 12/2004
WO WO 2014036551 A1 3/2014

OTHER PUBLICATIONS

German Office Action dated Mar. 14, 2016.

*Primary Examiner* — Vu Le
*Assistant Examiner* — Guillermo M Rivera-Martinez
(74) *Attorney, Agent, or Firm* — Harness, Dickey & Pierce, P.L.C.

(57) ABSTRACT

At least one first 3D image dataset of an examination region of interest of a patient and a second 3D image dataset of the examination region of interest are received via at least one first interface. A geometric model of the examination region of interest is determined based at least on the first 3D image dataset, and a first spatial distribution of a first material property of the examination region of interest is determined based at least on the second 3D image dataset. A digital manufacturing model of an object is generated based on the geometric model and on the first spatial distribution, the manufacturing model having a material composition of the object that is dependent on the first distribution. The manufacturing model therefore takes into account the geometry and the first material property of the examination region of interest.

26 Claims, 3 Drawing Sheets

(52) U.S. Cl.
CPC ........... *A61F 2002/30948* (2013.01); *A61F 2002/30952* (2013.01); *A61F 2002/30955* (2013.01); *A61F 2002/30962* (2013.01); *G06T 2200/04* (2013.01)

(56) References Cited

U.S. PATENT DOCUMENTS

| | | | |
|---|---|---|---|
| 2011/0142316 A1* | 6/2011 | Wang | G06T 11/006 382/131 |
| 2011/0196385 A1* | 8/2011 | Altrogge | G06F 19/12 606/130 |
| 2014/0222157 A1 | 8/2014 | Al Hares et al. | |
| 2014/0303629 A1 | 10/2014 | Lang et al. | |
| 2015/0146845 A1* | 5/2015 | Thibault | G06T 11/006 378/19 |

* cited by examiner

METHOD AND COMPUTING UNIT FOR GENERATING A MANUFACTURING MODEL

PRIORITY STATEMENT

The present application hereby claims priority under 35 U.S.C. § 119 to German patent application number DE 102015210984.4 filed Jun. 16, 2015, the entire contents of which are hereby incorporated herein by reference.

FIELD

At least one embodiment of the application generally relates to a method and/or a computing unit for generating a manufacturing model.

BACKGROUND

For the production of an implant it is desirable not only to realize a maximum possible degree of automation in order to deliver high levels of efficiency, but also to achieve a best possible match to the individual characteristics of the anatomy of the patient in question, which in theory is at odds with a total automation of the manufacturing process. The desire for a patient-specific anatomical adaptation applies in this case to such different implants as bone implants, a spinal disk replacement or cartilage structures for plastic or reconstructive surgery.

Especially in the case of an implant which is subjected to a constant load due to an interaction, for example as a result of movements, with one or more neighboring tissue structures, a detailed patient-specific matching of the implant to the surrounding tissue can preclude a deterioration of the implant on account of the load. Equally, this also enables undesirable retroactive effects caused by the implant on the tissue structures involved in the interaction to be reduced, thus helping to prevent inflammations, abrasion, indurations and physical wear and tear reactions of the tissue structures as a consequence of the implant.

WO 2004/110309 discloses a method which, in order to produce an implant, firstly acquires three-dimensional tomographic image data of the region of the body for which the implant is intended and generates a manufacturing model of the implant on the basis of said image data of the body region. Finally, the implant is fabricated with the aid of the manufacturing model produced on the basis of the tomographic image data. In WO 2014/036551, a method for the patient-specific embodiment of an implant is disclosed which utilizes three-dimensional tomographic image data in particular for determining two-dimensional contact areas of a bone implant with the bone designated for the implant.

Generally in the case of the cited methods, however, the image data is acquired using a single modality only, i.e. for example via computed tomography (CT) or magnetic resonance tomography (MRT), and then a manufacturing model of the implant is created directly by way of said image data generated by one modality. The result of this is that, in the generation of the manufacturing model, essentially only those anatomical structures of the body region in question are taken into account which are particularly effectively resolved by the modality used, i.e. bone structures in CT or soft tissue structures in MRT.

The above-described challenges extend not only to implants, but also to other objects for use in the medical engineering field. The object can in particular be a positioning aid for radiation planning or for surgery.

SUMMARY

At least one embodiment of the invention discloses a method for generating a manufacturing model for an object for use in the medical engineering field which enables a best possible matching of the object to the patient-specific anatomical characteristics.

At least one embodiment of the invention is directed to a method; at least one embodiment of the invention is directed to a computing unit; at least one embodiment of the invention is directed to an imaging device; at least one embodiment of the invention is directed to a computer program product; at least one embodiment of the invention is directed to a computer-readable medium; and at least one embodiment of the invention is directed to an object.

Inventive solutions are described hereinbelow in relation to embodiments of devices as well as methods. Features, advantages or alternative embodiment variants cited in this context are equally applicable to the other claimed subject matters also, and vice versa. In other words, the physical-type claims (which are directed for example to a device) may also be developed using the features that are described or claimed in connection with a method. The corresponding functional features of the method are in this case embodied by corresponding physical modules.

At least one embodiment of the invention is directed to a method for generating a manufacturing model of an object for use in the medical engineering field, comprising:

receiving at least one first 3D image dataset of an examination region of interest of a patient and a second 3D image dataset of the examination region of interest via at least one first interface, first determining of a geometric model of the examination region of interest based at least on the first 3D image dataset via a determination unit, second determining of a first spatial distribution of a first material property of the examination region of interest based at least on the second 3D image dataset via the determination unit, and generating a digital manufacturing model of the object based on the geometric model and on the first spatial distribution, wherein the manufacturing model has a material composition of the object that is dependent on the first spatial distribution.

At least one embodiment of the invention further relates to a computing unit for generating a manufacturing model of an object for use in the medical engineering field, comprising:

first interface, embodied for receiving at least one first 3D image dataset of an examination region of interest of a patient and a second 3D image dataset of the examination region of interest, determination unit, embodied for the first determining of a geometric model of the examination region of interest based at least on the first 3D image dataset via a determination unit, and for the second determining of a first spatial distribution of a first material property of the examination region of interest based at least on the second image dataset, and generation unit, embodied for generating a digital manufacturing model of the object based on the geometric model and on the first spatial distribution, wherein the manufacturing model has a material composition of the object that is dependent on the first distribution.

At least one embodiment of the invention also relates to a computer program product having a computer program and a computer-readable medium. An implementation largely in software has the advantage that computing units that have already been in use previously can also be easily upgraded via a software update in order to operate in the inventive manner. As well as the computer program, such a computer program product can if necessary comprise additional constituent parts such as e.g. documentation and/or additional components, including hardware components, such as e.g. hardware keys (dongles, etc.), in order to use the software.

BRIEF DESCRIPTION OF THE DRAWINGS

The invention is described and explained in more detail below with reference to the example embodiments illustrated in the figures. The example embodiments deal in particular with the case where the object is an implant. In further embodiment variants, the object is not an implant. In particular in further embodiment variants not described in more detail herein, the object can be a positioning aid for radiation planning or for surgery.

In the figures.

DETAILED DESCRIPTION OF THE EXAMPLE EMBODIMENTS

Figure 1:
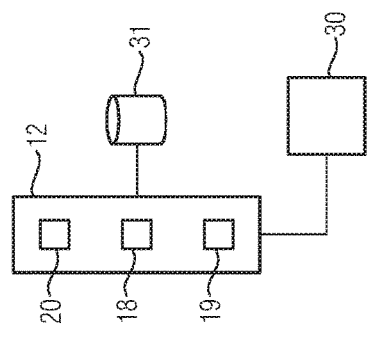
FIG. 1 shows a computing unit.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A first embodiment of the invention is based on the fact that at least one first 3D image dataset of an examination region of interest of a patient and also a second 3D image dataset of the examination region of interest are received via at least one first interface. The inventors have recognized that a geometric model of the examination region of interest can be determined based at least on the first 3D image dataset, and a first spatial distribution of a first material property of the examination region of interest can be determined based at least on the second 3D image dataset. Based on the geometric model and on the first spatial distribution, a digital manufacturing model of an object can be generated for use in the medical engineering field, the manufacturing model having a material composition of the object that is dependent on the first distribution. The manufacturing model therefore takes into account the geometry and the first material property of the examination region of interest, with the result that the object based on the manufacturing model is matched to a great extent to the patient-specific anatomical characteristics.

The geometric model comprises information about the structure of the examination region of interest, in particular about at least one surface or boundary surface of at least one part of the examination region of interest. The manufacturing model includes information about the structure of the object, in particular about the surface of the object. The information about the structure of the object can be determined as a function of the geometric model; in particular, the structure of the object can be determined as a negative shape or as a replacement for a structure in the geometric model.

The object can be produced by way of a 3D printer. Such a 3D printer generates the object directly in accordance with the prototype of the manufacturing model, in particular via CAD (acronym for Computer Aided Design). Different production materials can be used in order to generate the object, in particular ceramics, metals, plastics and synthetic resins. In this case different production materials can be joined to one another by way of a melting or gluing process. Special variants of 3D printing are selective laser melting or electron beam melting for metals and selective laser sintering for plastics, ceramics and metals. As far as the present invention is concerned, the (poly)jet method is particularly advantageous. This entails depositing a plurality of layers, in particular of one or more plastics and/or synthetic resins, via one or more jets. A 3D printer can therefore have one or more jets for laying down layers, in particular of a plastic and/or of a synthetic resin. The manufacturing model can therefore comprise information about the layer thickness of individual layers which are to be applied by way of a (poly)jet method.

Furthermore, the following technical terms are known for variants of 3D printing: ballistic layer manufacturing, cladding, computer numerical control, contour crafting, digital light processing, direct laser forming, direct manufacturing, direct metal deposition, direct metal laser sintering, direct shell production casting, electron beam melting, electron beam projection lithography, electrophoretic deposition, fused deposition modeling, ink-jet deposition, laminated object manufacturing, laser ablation, laser engineered net shaping, laser metal forming, laser powder forming, laser-Cusing, microfabrication, multi-jet modeling, multiphoton lithography, photolithography, plaster-based 3D printing, robocasting, selective fusing, selective laser melting, selective laser sintering, solid ground curing, spin casting, stereolithography.

The object can be in particular an implant. The implant can be a replacement for a bone or cartilage structure, a spinal disk, an organ or a part of an organ, for example a cardiac valve or a stent, in particular for blood vessels. The implant is preferably fabricated from biocompatible production materials or coated with such. The implant can therefore be produced in such a way that a 3D printer at least partially applies biological production material. In a variant of the invention, biological production material is at least partially deposited by way of the (poly)jet method. Furthermore, the implant can include additional functions via chemical treatment and/or a treatment of the surface. For example, the implant can have pharmacologically active substances such that these are released into the patient's bloodstream.

According to a further embodiment of the invention, the first 3D image dataset is a CT dataset acquired at a first X-ray energy, while the second 3D image dataset is a CT dataset acquired at a second X-ray energy. In this case the first X-ray energy is different from the second X-ray energy. Furthermore, in the case of this embodiment, the second determination is based both on the first and on the second 3D image dataset. Scanning the examination region of interest at different X-ray energies namely permits materials in the examination region of interest to be identified, bone and soft tissue structures in particular being readily distinguishable. Furthermore, this also enables the concentrations of materials to be determined. For example, the bone density can be determined in this way.

According to a further embodiment of the invention, the first 3D image dataset has a higher spatial resolution than the second 3D image dataset. Owing to the high spatial resolution, the first 3D image dataset is particularly well suited for determining a geometric model of the examination region of interest. However, the same high spatial resolution is not necessarily required in order to determine the first spatial distribution of the first material property. In particular, the first 3D image dataset may have been acquired via a different imaging modality than the second 3D image dataset.

According to a further embodiment of the invention, the first material property is a mechanical property. Matching the object is namely particularly successful when the manufacturing model has a material composition of the object that is dependent on the mechanical property of the examination region of interest. The manufacturing model therefore has such a material composition of the object that the latter is matched to the patient-specific anatomical characteristics.

According to a further embodiment of the invention, the mechanical property relates to elasticity, density, strength or hardness. Within the meaning of the present application, elasticity can be a bulk modulus, a modulus of rigidity or a modulus of elasticity. With regard to strength, it can be in particular tensile strength, pressure resistance, compressive strength, flexural strength, torsional strength or shear strength.

According to a further embodiment of the invention, the method for generating a manufacturing model also comprises the step of classifying subregions of the examination region of interest based on the first spatial distribution. In this case the subregions can be assigned to different tissue classes. Furthermore, specific classes of subregions, in particular of tissues, can be assigned to specific material properties.

According to a further embodiment of the invention, the manufacturing model is generated in such a way that the material composition of the object corresponds to the first spatial distribution. The spatial distribution then corresponds to a 3D distribution of production materials. In particular, the manufacturing model can be generated by the establishing of a functional relationship between the material composition of the object and the first spatial distribution. Such a functional relationship may be predefined by default or can be selected by a user.

According to a further embodiment of the invention, the method for generating a manufacturing model comprises the step of simulating a load on the examination region of interest, the material composition being determined as a function of the simulation. Typically, the simulation is based on the geometric model as well as on the first spatial distribution. Based on the simulated load, it is possible to derive requirements that are to be fulfilled by the material composition. In this case a static and/or a dynamic load can be simulated. The simulation can be implemented numerically. The simulation can be performed using FEM methods (FEM=acronym for Finite Element Modeling), finite differences methods, finite volume methods or with the aid of the lattice-Boltzmann method.

Furthermore, the manufacturing model can be generated in such a way that the material composition is inhomogeneous and/or anisotropic. In particular, the manufacturing model can have a gradient of at least two different production materials. Furthermore, an inhomogeneous and/or anisotropic material composition can also produce an inhomogeneous and/or anisotropic mechanical property of the object.

According to a further embodiment of the invention, the manufacturing model is generated by way of a database, an assignment of a plurality of different first material properties to production materials being stored in the database. In particular, a material property can be assigned to a specific mix of production materials. This enables the material composition of the object to be determined in a particularly simple and reliable manner.

According to a further embodiment of the invention, the method for generating a manufacturing model comprises the steps of transferring the manufacturing model to a 3D printer and of printing the object based on the manufacturing model via the 3D printer. The manufacturing model can be transferred in particular via the first interface or via a further, second interface.

According to a further embodiment of the invention, the manufacturing model is transferred to the 3D printer via a network. This enables the object to be produced at different locations. The manufacturing model can comprise all the necessary information for generating the object. However, the manufacturing model can also be modified after the transfer. For example, the manufacturing model can be present in STL (acronym for Surface Tessellation Language) or AMF (acronym for Additive Manufacturing Format). In particular, the network can be an intranet or the internet.

At least one embodiment of the invention further relates to a computing unit for generating a manufacturing model of an object for use in the medical engineering field, comprising:

first interface, embodied for receiving at least one first 3D image dataset of an examination region of interest of a patient and a second 3D image dataset of the examination region of interest, determination unit, embodied for the first determining of a geometric model of the examination region of interest based at least on the first 3D image dataset via a determination unit, and for the second determining of a first spatial distribution of a first material property of the examination region of interest based at least on the second image dataset, and generation unit, embodied for generating a digital manufacturing model of the object based on the geometric model and on the first spatial distribution, wherein the manufacturing model has a material composition of the object that is dependent on the first distribution.

Such a computing unit can be embodied in particular for performing the above-described methods according to the invention and their aspects. The computing unit is embodied for performing said methods and their aspects by virtue of the first interface, the determination unit and the generation unit being embodied for performing the corresponding method steps. In a further embodiment variant of the invention, the computing unit also has a second interface and the 3D printer in order to transfer and print the manufacturing model. The invention further relates to an imaging device, embodied for acquiring the first and/or the second 3D image dataset, having a computing unit according to the invention.

The first 3D image dataset is different from the second 3D image dataset. For example, the two 3D image datasets may been acquired using different imaging devices or using different acquisition parameters. An imaging device can be a tomographic device, in particular a computed tomography device or a magnetic resonance tomography device. Furthermore, an imaging device can be an X-ray apparatus such as a C-arm X-ray device. An imaging device can also be an ultrasound device which is configured to acquire a 3D image dataset. An ultrasound device can acquire a 3D image dataset in particular by way of what is termed Doppler sonography. Furthermore, a 3D image dataset can also be produced by way of diffusion imaging.

A 3D image dataset can comprise multiple 3D images of the examination region of interest that have been acquired at different time instants. The 3D images can be in particular tomographic images. Thus, during the acquisition of a 3D image dataset, a plurality of measured data is acquired at different time instants via a tomographic device. From said measured data, 3D images having different time-related focal points can be reconstructed. Accordingly, it is necessary to assign the reconstructed 3D images to different time instants. The measured data for the 3D image dataset can be acquired in particular during a single scan.

Within the scope of the present application, "3D" serves to designate a spatially three-dimensional property. If a 3D image dataset comprises multiple 3D images acquired at different time instants, then said 3D image dataset can also be described as a 4D image dataset. In this case "4D" denotes a spatially three-dimensional as well as a temporal property. Thus, a 4D image dataset also comprises a 3D image dataset.

At least one embodiment of the invention also relates to a computer program product having a computer program and a computer-readable medium. An implementation largely in software has the advantage that computing units that have already been in use previously can also be easily upgraded via a software update in order to operate in the inventive manner. As well as the computer program, such a computer program product can if necessary comprise additional constituent parts such as e.g. documentation and/or additional components, including hardware components, such as e.g. hardware keys (dongles, etc.), in order to use the software.

The computing units shown here and the imaging device shown here are configured to perform a method according to the invention. FIG. 1 shows a computing unit. The computing unit shown here comprises a first interface 19, a determination unit 18 and a generation unit 20 and is connected to a 3D printer 30. An interface refers to generally known hardware or software interfaces, for example the hardware interfaces PCI bus, USB or Firewire. Both the determination unit 18 and the generation unit 20 can have software elements and hardware elements, for example a microprocessor or a device called an FPGA (acronym for "Field Programmable Gate Array"). The determination unit 18, the interface 19 and the generation unit 20 can each be embodied as a component part of a computer 12. Furthermore, the computing unit can communicate with a database 31. The computing unit can have further interfaces, in particular for communication with the database 31 and with the 3D printer 30.

Figure 2:
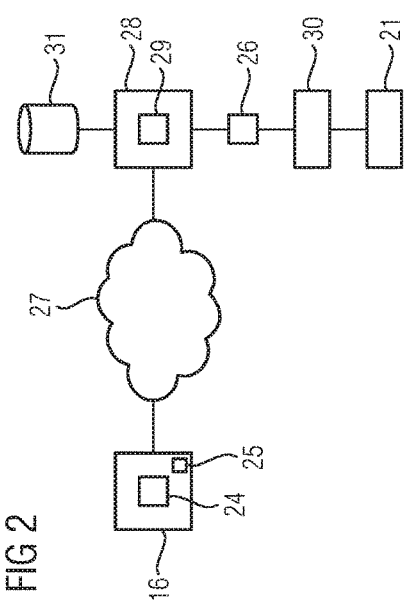
FIG. 2 shows a network including a computing unit.

FIG. 2 shows a network including a computing unit. The first 3D image dataset 24 and the second 3D image dataset 25 are stored on a server 16 and can be transferred to the client 28 via a network 27. In the embodiment variant shown here, said client 28 is embodied as a computing unit. A computer program 29 is stored in executable form on the client 28. The client 28 has access to a database 31 in which a plurality of production materials associated with specific material properties are stored. In the example embodiment shown here, the calculated manufacturing model 26 is transferred directly to a 3D printer 30. In a further example, not shown here, the manufacturing model 26 is transferred back to the server 16 or to a different client. At the same time the transfer TRF of the manufacturing model 26 to the 3D printer 30 can also take place via a network 27. Accordingly, the 3D printer 30 can also be connected to the server 16 or to a different client.

Figure 3:
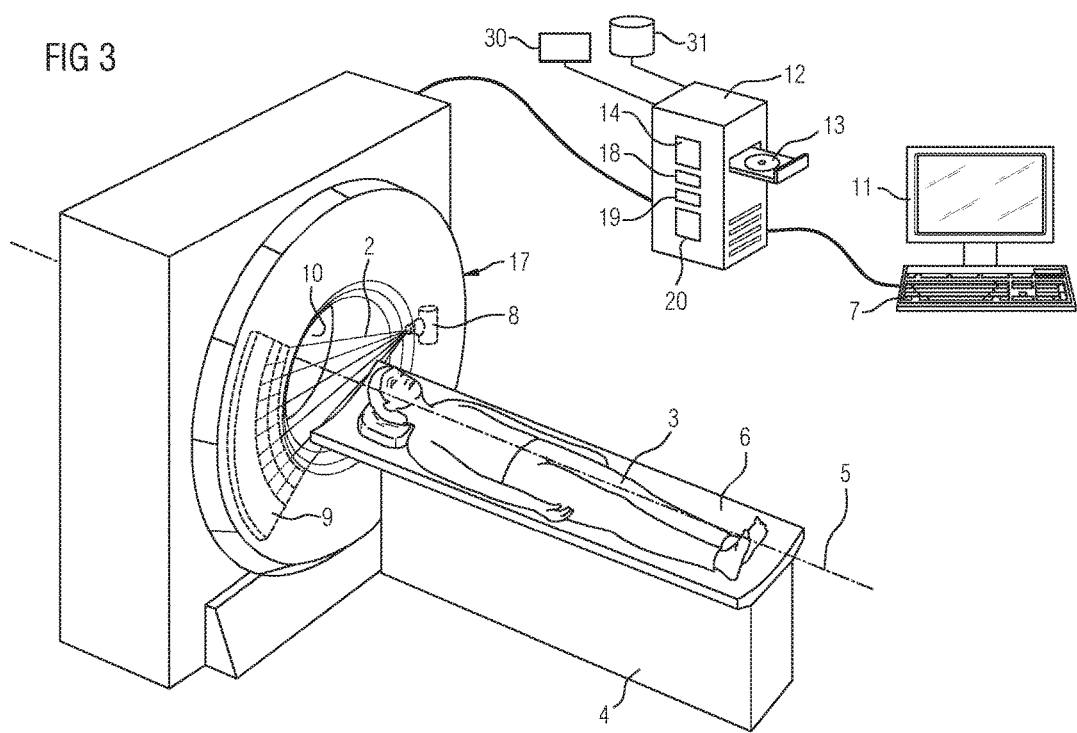
FIG. 3 shows an imaging device.

FIG. 3 shows an imaging device based on the example of a computed tomography device. The computed tomography device shown here features a scanning unit 17, comprising an X-ray source 8 and an X-ray detector 9. During the acquisition of measured data, the scanning unit 17 rotates about a system axis 5, and during the acquisition the X-ray source 8 emits X-ray beams 2. In the example shown here, the X-ray source 8 is an X-ray tube. In the example shown here, the X-ray detector 9 is a row detector having a plurality of rows. The imaging device may furthermore be a computed tomography device having a plurality of X-ray sources 8 and X-ray detectors 9 that are paired with one another. Such devices are suitable in particular for acquiring 3D image datasets at different X-ray energies.

X-ray sources 8 for imaging have a spectrum of X-ray beams, where each spectrum corresponds to a defined X-ray energy. For example, one spectrum corresponds to the mean X-ray energy of this spectrum. A spectrum or an X-ray energy can also be defined by way of a setting of the X-ray tube, in particular by way of a voltage of the X-ray tube. For example, the first 3D image data 25 can be recorded at an X-ray tube voltage of 80 kV, and the second 3D image data at an X-ray tube voltage of 120 kV. A 3D image dataset recorded at a defined X-ray energy therefore denotes a 3D image dataset that has been acquired with a spectrum corresponding to said defined X-ray energy.

Furthermore, the X-ray detector 9 can be embodied as a counting detector. A counting detector can determine the number of photons detected. Furthermore, the X-ray detector 9 can be embodied as an energy-resolving detector. An energy-resolving detector can assign the detected X-ray radiation to one of at least two different X-ray energies. An energy-resolving detector enables two CT datasets to be acquired at different energy via one X-ray tube operated at constant voltage.

In the example shown here, a patient 3 lies on a patient couch 6 during the acquisition of measured data. The patient couch 6 is connected to a couch base 4 such that the latter supports the patient couch 6 together with the patient 3. The patient couch 6 is configured to move the patient 3 along a scanning direction through the bore 10 of the scanning unit 17. The scanning direction is generally given by the system axis 5, about which the scanning unit 17 rotates when recording measured data. In a spiral scan, the patient couch 6 is moved continuously through the bore 10 while the scanning unit 17 rotates around the patient 3 and captures measured data. The X-ray beams 2 accordingly describe a spiral on the surface of the patient 3. For the reconstruction of 3D images based on the measured data, the computed tomography device shown here additionally features a reconstruction unit 14.

In addition, an imaging device like the computed tomography device shown here can also feature a contrast agent injector for injecting contrast agent into the bloodstream of the patient 3. This enables the 3D images to be recorded using a contrast agent in such a way that an examination region of interest perfused with blood can be visualized with an enhanced contrast. Furthermore, the contrast agent injector also affords the possibility of actuating angiographic acquisitions or of performing a perfusion scanning sequence. By contrast agents are generally understood such agents which enhance the visualization of structures and functions of the body in imaging methods. Within the scope of the present application, both conventional contrast agents such as iodine or gadolinium, for example, and tracers such as 18F, 11C, 15O or 13N, for example, are to be understood here by contrast agents.

In the example shown here, the first interface 19 is embodied as part of the computer 12. The computer 12 is connected to an output unit in the form of a screen 11 as well as to an input unit 7. The 3D images can be presented on the screen in a variety of forms, for example as rendered volume images or as sectional images (slices). The input unit 7 is for example a keyboard, a mouse, a "touchscreen" or even a microphone for voice input. A computer program 29 according to the invention can be launched via the input unit 7. The individual steps of the method according to the invention can be supported by the input unit 7; for example, a selection of an examination region of interest in a 3D image can be confirmed via a mouse click.

The computed tomography device shown here has a reconstruction unit 14 for reconstructing 3D images. The computer 12 also comprises a determination unit 18 and a generation unit 20. The computer 12 and the units associated therewith can cooperate with a computer-readable medium 13, in particular in order to perform a method according to the invention via a computer program 29 containing program code. Furthermore, the program code of the computer program 29 can be stored in retrievable form on the machine-readable medium 13. In particular, the machine-readable medium can be a CD, DVD, Blu-ray Disc, a memory stick or a hard disk. In this case the computer program product comprises the computer program 29 and the corresponding program code.

In the embodiment variant shown here, at least one computer program 29 is stored in the memory of the computer 12 and performs all of the method steps of the method according to the invention when the computer program 29 is executed by the computing unit. The computer program 29 for performing the method steps of the method according to the invention comprises program code. Furthermore, the computer program 29 can be embodied as an executable file and/or be stored on a different computing system from the computer 12. For example, the computing unit can be configured such that the computer program 29 is loaded into the memory of the computing unit via an intranet or via the internet in order to perform the method according to the invention.

In a further embodiment variant, the first 3D image dataset 24 and the second 3D image dataset 25 are acquired via different imaging devices. Thus, the first 3D image dataset 24 can be acquired using an imaging device having a high spatial and/or temporal resolution, for example via a CT device. The second 3D image dataset 25 can then be acquired using an imaging device having a less high resolution. In particular, the second 3D image dataset 25 can be an elastographic image dataset. Elastography is based on sonography or magnetic resonance tomography and permits the elasticity of the at least one part of the examination region of interest to be determined.

Figure 4:
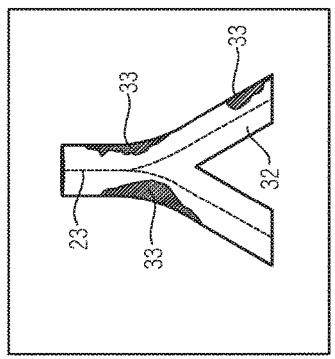
FIG. 4 shows a 3D image of an examination region of interest.

FIG. 4 shows a 3D image of an examination region of interest. In the example shown here, the examination region of interest is a vessel section, and specifically a part of the aorta in the abdominal cavity. In this case the 3D image is presented in the form of a sectional image or slice in the frontal plane. The dashed line 23 marks the midline of the vessel section. In the example shown here, an unobstructed blood flow is restricted by plaques 33. A stenosis 32, i.e. a constriction of the vessel section, is therefore present. These plaques 33 have different material properties from the walls of the vessel section. The examination region of interest shown here is an important afferent blood vessel, so it is desirable to treat the stenosis 32 in such a way that the hemodynamic properties of the examination region of interest are altered via an implant 21 in the form of a stent in such a way that they correspond to those of a healthy patient 3. The stent is therefore intended on the one hand to support the examination region of interest and on the other hand to influence the hemodynamic properties. The hemodynamic properties can be influenced in particular by way of the elasticity of the stent. The elasticity of the stent is in turn influenced by the material composition of the stent. The invention described herein therefore permits an implant 21 to be produced in such a way that the latter is individually matched to the anatomy of the patient 3 and as a result the function of the examination region of interest is improved.

Figure 5:
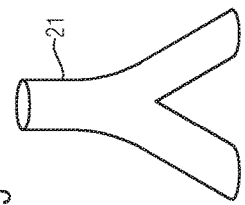
FIG. 5 shows an object based on the example of an implant.
Figure 6:
FIG. 6 shows a flowchart of a method for producing an object.

FIG. 5 shows an object based on the example of an implant. In this case the implant is embodied in the form of a stent. Said implant is suited in particular to support or to replace the examination region of interest shown in FIG. 4. An object according to the invention can be produced using the method illustrated in FIG. 6. The method illustrated in FIG. 6 is described in more detail using an implant as example. However, the method illustrated in FIG. 6 can also be applied to objects other than an implant. This method can optionally also include the acquisition IMG of a first 3D image dataset 24 and of a second 3D image dataset 25. In this case the acquisition IMG also comprises the reconstruction of 3D images. The generation of a manufacturing model is based on the receiving REC of the first 3D image dataset 24 via a first interface 19, wherein the first 3D image dataset 24 comprises 3D images of an examination region of interest of a patient 3. There now follows a first determining DET-1 of a geometric model of the examination region of interest based at least on the first 3D image dataset 24 via a determination unit 18, and a second determining DET-2 of a first spatial distribution of a first material property of the examination region of interest based at least on the second 3D image dataset 25 via the determination unit 18.

Both the first determining DET-1 and the second determining DET-2 can be based in each case on the segmentation of at least a part of the examination region of interest. Conventional algorithms, such as a region-oriented algorithm or an edge-oriented algorithm, can be used for the segmentation. Furthermore, the segmentation step can be based on a midline 23 of an examination region of interest, in particular of a vessel section. Furthermore, the structures segmented in different 3D images or 3D image datasets can be registered with one another. For example, a first structure can be segmented in the first 3D image dataset 24, and a second structure in the second image dataset 25. These two structures can now be registered with one another, in particular in order to determine the first geometric model and/or the first spatial distribution. Furthermore, the first 3D image dataset 24 and the second 3D image dataset 25 can also be registered with one another prior to the segmentation step.

The calculation CAL of a manufacturing model 26 of an implant 21 based on the geometric model and on the first spatial distribution is now carried out, the manufacturing model 26 having a material composition of the implant 21 that is dependent on the first spatial distribution. In particular, the manufacturing model 26 can have a spatial distribution of production materials for producing the implant 21. This manufacturing model 26 can define properties of the implant 21, such as its material characteristics, the thickness of individual constituent parts of the implant, etc. The manufacturing model 26 is typically embodied as a 3D model and describes both the 3D geometry of the implant and the 3D material composition of the implant 21.

Furthermore, the calculation CAL can be based on the classification CLF of subregions of the examination region of interest based on the first spatial distribution. In this case subregions can be assigned in particular to different material classes. For example, a first spatial distribution of the elasticity and/or an X-ray absorption property can be determined first. Furthermore, the elasticity and/or the X-ray absorption property can be assigned to specific subregions of the examination region of interest, in particular based on a segmentation of said subregions. These subregions can then be grouped into classes according to their elasticity and/or X-ray absorption property. The classes can be tissue classes. Such classes can be "bone", "cartilage", "muscle tissue". The subregions can also be divided into subclasses, for example "bone with reduced bone density".

Furthermore, the calculation CAL can be based on the simulation SIM of a load on the examination region of interest, the material composition being determined as a function of the simulation. The load can be simulated statically or dynamically. In particular, the load can be simulated taking into account an interaction with tissue adjoining the examination region of interest. Furthermore, the first spatial distribution of a first material property can be determined in such a way that the spatial distribution withstands a simulated load. This enables the manufacturing model 26 to be individually matched to the anatomy of the patient 3.

Optionally, a step of modification MOD of the manufacturing model 26 can be performed. The modification MOD can be carried out based on an input by a user of the computing unit or based on predefined boundary conditions. The input can bring about a direct modification MOD of the manufacturing model 26, for example in that the thickness of a structure of the implant 21 is adjusted. Furthermore, the step of displaying PIC the manufacturing model 26 can optionally be carried out. For example, the manufacturing model 26 can be displayed on a display unit 11. The modification MOD can be accomplished by way of an interaction of the user by way of an input unit 7 and the display unit 11 with the displayed manufacturing model 26. For example, an area of the displayed manufacturing model 26 can be marked and the marked area shifted. The modification MOD can also comprise a scaling of the manufacturing model 26.

The manufacturing model 26 can be present in different formats or be converted into different formats. In particular, the manufacturing model 26 can be present in the STL format. The manufacturing model 26 can now be transferred to the 3D printer 30, for example by transfer TRF via a network 27. There then follows the production PRT of an implant 21 based on the manufacturing model 26 via a 3D printer 30. In this case the 3D printer 30 converts the information concerning the structure, the material composition, etc. of the manufacturing model 26 into an implant 21 via a printing process.

In further embodiment variants of the invention, the term "based on" can be replaced by "as a function of" or "functionally dependent on".

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating a digital manufacturing model of an object for use in medical engineering, comprising:
   determining a geometric model of an examination region of interest of a patient based on a first three-dimensional (3D) image dataset of the examination region of interest;
   determining a spatial distribution of a material property of the examination region of interest based on a second 3D image dataset of the examination region of interest; and
   generating the digital manufacturing model of the object based on the geometric model and the spatial distribution, the digital manufacturing model representing a material composition of the object, the generating the digital manufacturing model including determining an association between the spatial distribution and one or more production materials included in the material composition.

2. The method of claim 1, wherein
   the first 3D image dataset is a computed tomography (CT) dataset acquired at a first X-ray energy, and
   the second 3D image dataset is a CT dataset acquired at a second X-ray energy.

3. The method of claim 1, wherein the first 3D image dataset has a higher spatial resolution than the second 3D image dataset.

4. The method of claim 1, wherein the material property is a mechanical property.

5. The method of claim 4, wherein the mechanical property includes one of the following properties: elasticity, density, strength, or hardness.

6. The method of claim 1, further comprising:
   classifying subregions of the examination region of interest based on the spatial distribution.

7. The method of claim 6, wherein the classifying classifies different tissues of the subregions.

8. The method of claim 1, further comprising:
   simulating a load on the examination region of interest, wherein the material composition is determined based on the simulating.

9. The method of claim 1, wherein the generating generates the digital manufacturing model using a database, the database storing associations between each of a plurality of different material properties and respective production materials of a plurality of different production materials, the plurality of different material properties including the material property, and the plurality of different production materials including the one or more production materials.

10. The method of claim 1, further comprising:
    transferring the digital manufacturing model to a 3D printer; and
    producing the object based on the digital manufacturing model via the 3D printer.

11. A computing unit for generating a digital manufacturing model of an object for use in medical engineering, comprising:
    a determination unit configured to
      determine a geometric model of an examination region of interest of a patient based on a first three-dimensional (3D) image dataset of the examination region of interest, and
      determine a spatial distribution of a material property of the examination region of interest based on a second 3D image dataset of the examination region of interest; and
    a generation unit configured to generate the digital manufacturing model of the object based on the geometric model and the spatial distribution, the digital manufacturing model representing a material composition of the object, the generation of the digital manufacturing model including determining an association between the spatial distribution and one or more production materials included in the material composition.

12. An imaging device configured to acquire at least one of the first 3D image dataset and the second 3D image dataset, comprising:
    the computing unit of claim 11.

13. At least one imaging device configured to acquire the first 3D image dataset and the second 3D image dataset, comprising:
    the computing unit of claim 11,
    wherein the first 3D image dataset is a computed tomography (CT) dataset acquired at a first X-ray energy, and the second 3D image dataset is a CT dataset acquired at a second X-ray energy.

14. A non-transitory computer-readable medium, including program sections that, when executed by a computing unit, cause the computing unit to perform the method of claim 1.

15. An object for use in medical engineering, produced via the method of claim 1.

16. The method of claim 2, wherein the first 3D image dataset has a higher spatial resolution than the second 3D image dataset.

17. The method of claim 2, wherein the material property is a mechanical property.

18. The method of claim 17, wherein the mechanical property includes one of the following properties: elasticity, density, strength, or hardness.

19. The method of claim 2, wherein the generating generates the digital manufacturing model using a database, the database storing associations between each of a plurality of different material properties and respective production materials of a plurality of different production materials, the plurality of different material properties including the material property, and the plurality of different production materials including the one or more production materials.

20. An apparatus for generating a digital manufacturing model of an object for use in medical engineering, comprising:
    one or more processors configured to execute computer readable instructions to
        determine a geometric model of an examination region of interest of a patient based on a first three-dimensional (3D) image dataset of the examination region of interest,
        determine a spatial distribution of a material property of the examination region of interest based on a second 3D image dataset of the examination region of interest, and
        generate the digital manufacturing model of the object based on the geometric model and the spatial distribution, the digital manufacturing model representing a material composition of the object, the generation of the digital manufacturing model including determining an association between the spatial distribution and one or more production materials included in the material composition.

21. The apparatus of claim 20, further comprising:
    a memory storing the computer readable instructions.

22. An imaging device configured to acquire at least one of the first 3D image dataset and the second 3D image dataset, comprising:
    the apparatus of claim 20.

23. At least one imaging device configured to acquire the first 3D image dataset and the second 3D image dataset, comprising:
    the apparatus of claim 20,
        wherein the first 3D image dataset is a computed tomography (CT) dataset acquired at a first X-ray energy, and the second 3D image dataset is a CT dataset acquired at a second X-ray energy.

24. A non-transitory computer-readable medium, including program sections that, when executed by a computing unit, cause the computing unit to perform the method of claim 3.

25. The method of claim 1, wherein the digital manufacturing model defines specifications of the object for use by a manufacturing device when manufacturing the object, the specifications including the material composition.

26. The method of claim 1, wherein the object is an implant.

* * * * *